(12) United States Patent
Neuberger

(10) Patent No.: US 10,456,590 B2
(45) Date of Patent: Oct. 29, 2019

(54) DEVICE AND METHOD FOR LASER TREATMENTS

(71) Applicant: Biolitec Pharma Marketing Ltd., F.T. labuan (MY)

(72) Inventor: Wolfgang Neuberger, Dubai (AE)

(73) Assignee: Biolitec Unternehmensbeteiligungs II AG, Vienna (AT)

( * ) Notice: Subject to any disclaimer, the term of this patent is extended or adjusted under 35 U.S.C. 154(b) by 674 days.

(21) Appl. No.: 14/441,786

(22) PCT Filed: Nov. 11, 2013

(86) PCT No.: PCT/IB2013/002504
§ 371 (c)(1),
(2) Date: May 11, 2015

(87) PCT Pub. No.: WO2014/072806
PCT Pub. Date: May 15, 2014

(65) Prior Publication Data
US 2015/0305811 A1 Oct. 29, 2015

Related U.S. Application Data

(60) Provisional application No. 61/724,700, filed on Nov. 9, 2012.

(51) Int. Cl.
*A61N 5/06* (2006.01)
*A61B 18/20* (2006.01)
(Continued)

(52) U.S. Cl.
CPC .......... *A61N 5/0616* (2013.01); *A61B 18/203* (2013.01); *A61B 18/22* (2013.01);
(Continued)

(58) Field of Classification Search
CPC ............ A61N 5/062; A61N 2005/0626; A61N 2005/063; A61N 2005/067; A61B 18/12; A61B 18/203
See application file for complete search history.

(56) References Cited

U.S. PATENT DOCUMENTS 5,570,445 A * 10/1996 Chou ................... G02B 6/4296
385/78
6,110,195 A * 8/2000 Xie ....................... A61B 18/203
606/10

(Continued)

*Primary Examiner* — Amanda K Hulbert
*Assistant Examiner* — Roland Dinga
(74) *Attorney, Agent, or Firm* — BJ Associates; Bolesh J. Skutnik

(57) ABSTRACT

Improved, efficient devices/methods for medical and cosmetic applications, involving the delivery of laser energy to tissue are provided. In a preferred embodiment a portable, easy-to-use laser system comprises at least one laser source operating at one or more laser wavelengths; an electronic visual display having a n-dimensional input interface to set/select laser parameters; and at least one waveguide optically coupled to the laser source to convey laser radiation to a treatment site. The n-dimensional input interface inputs/selects lasing parameters which allows the selection of a combination of output wavelengths and powers by simply touching the electronic visual display. Method of use comprises the steps of placing at least one waveguide at preselected treatment site; selecting a combination of laser wavelengths and power by interacting with an electronic visual display; and irradiating the treatment site.

15 Claims, 2 Drawing Sheets

(51) Int. Cl.
*A61B 18/22* (2006.01)
*A61B 18/00* (2006.01)
*A61N 5/067* (2006.01)
*A61B 17/00* (2006.01)

(52) U.S. Cl.
CPC .... *A61N 5/062* (2013.01); *A61B 2017/00482* (2013.01); *A61B 2018/00452* (2013.01); *A61B 2018/00696* (2013.01); *A61B 2018/00958* (2013.01); *A61B 2018/2065* (2013.01); *A61B 2018/205547* (2017.05); *A61N 2005/063* (2013.01); *A61N 2005/067* (2013.01); *A61N 2005/0626* (2013.01)

(56) References Cited

U.S. PATENT DOCUMENTS

| | | | | |
|---|---|---|---|---|
| 8,537,203 B2 * | 9/2013 | Seibel | ............. | A61B 1/0008 348/45 |
| 2009/0105698 A1 * | 4/2009 | Hodel | ............. | A61B 18/22 606/11 |
| 2010/0010482 A1 * | 1/2010 | Neuberger | ............. | A61N 5/062 606/10 |
| 2010/0251154 A1 * | 9/2010 | Chang | ............. | G06F 3/0488 715/769 |
| 2012/0327122 A1 * | 12/2012 | Imamura | ............. | G06F 3/04815 345/649 |
| 2013/0227490 A1 * | 8/2013 | Thorsander | ............. | G06F 3/0482 715/841 |

\* cited by examiner

DEVICE AND METHOD FOR LASER TREATMENTS

CROSS REFERENCE TO PRIORITY APPLICATION

This patent application claims priority to U.S. provisional patent application No. 61/724,700, filed 9 Nov. 2012, by Wolfgang Neuberger/Biolitec Pharma Marketing Ltd entitled, "DEVICE AND METHOD FOR LASER TREATMENTS" which is hereby expressly incorporated by reference in its entirety as part of the present disclosure.

BACKGROUND OF THE INVENTION

Field of the Invention

The present invention relates to surgical instruments, devices and methods for transferring electromagnetic radiation to a mammalian body; and more particularly to devices and methods for medical or cosmetic applications applying laser radiation.

Invention Disclosure Statement

Laser devices have shown many advantages in comparison with other technologies for medical and cosmetic applications where light of the required spatial or temporal coherence could not be produced using simpler technologies. Since the discovery of laser technology for medical applications, there has been a variety of improved and specialized laser types, however these prior art laser systems show several disadvantages compared to other approaches. One of them is the dimensions of prior art laser equipments which are bulky, heavy and difficult to transport, even within hospitals. The bigger the equipment, the higher the number of physical, electronic and electrical components of these lasers and hence more time and money are spent on frequent maintenance and calibration procedures. Additionally, these lasers provide only a limited wavelength range which can only produce a limited diversity of therapeutic effects. Thus, high costs and limited range of therapeutic effects for a single device lead to expensive and less effective laser surgeries. Therefore, to increase the effectiveness of the laser treatment, multiple prior art laser devices could be required, raising even further the price of laser treatments. In addition, the need of using several laser devices for one effective treatment increases enormously the complexity and time of the procedure, as well as its costs. In an attempt to overcome these disadvantages, European Application Publication No. 1279375A1 by Colles et al. discloses a portable laser system for medical applications comprising light generating means, control means and power supply means, wherein the power supply comprises a battery. Even though portability is improved, so that it might prevail over bulkier prior art laser devices, its size and the still limited number of medical applications that the device can perform leave unaddressed needs which are addressed with the present invention.

Another example of a portable semiconductor diode laser for medical treatment is disclosed in US patent Publication No. 2011/0040358 A1 by Bean et al. It is a compact and lightweight laser device however its application is limited to the use of a single laser wavelength and hence the versatility of the system is diminished. Another example is a multipurpose portable laser depilation apparatus disclosed in the International application No. WO 2011/107628 A1 by Gomez de Diego which operates at one, two or three laser wavelengths, 808 nm for dark hair and 685 nm for light hair and 1054 nm for dark hair and skin. However, the capability and versability of the portable laser device disclosed therein is limited as it can operate at only a single laser wavelength at a time and with a predetermined output power, defined by the laser wavelength in use. Thus, it is not possible to obtain with this laser device a combined, enhanced and efficient therapeutic effect by using different laser wavelengths in a single, concurrent treatment. Additionally, as the output power is determined by the selected laser wavelength in use, the therapeutic effect is still limited.

An unfulfilled desired advantage over prior art laser devices for medical applications would be the possibility of delivering more than one laser wavelength in a single, concurrent treatment and having the ability to choose the output power, for each treatment, to enhance and better control the therapeutic effect by using multiple laser wavelengths concurrently with output powers of the different wavelength determined by the physician according to needs of the treatment. All this versatility would ideally be present in a small, compact, lightweight, portable laser device. There is therefore a need for an improved and efficient method and device for medical and cosmetic applications, involving the delivery of laser energy to the tissue in an efficient manner and providing more than one therapeutic effect. The enhanced device should be safe, simple to use and small in comparison with prior art devices, while effectively delivering laser energy to tissue. Present invention addresses these needs by providing compact, portable, easy-to-use laser devices, which in turn reduce costs while at the same time providing a versatile, safe and efficient laser energy delivery to perform medical treatments for patients.

OBJECTIVES AND BRIEF SUMMARY OF THE INVENTION

It is an objective of the present invention to provide a new generation of laser systems for medical and cosmetic applications including dermatology, ENT, gynecology, proctology, phlebology, pneumology, gastroenterology, ophthalmology, spinal disk surgery, thoracic surgery, general laser surgery, photodynamic therapy, lipo surgery and urology treatments.

It is also an objective of the present invention to provide laser devices that enable incision, excision, vaporization, ablation, hemostasis, disruption/destruction, chromophore/photosensitizer activation, and/or coagulation to be performed selectively and accurately in soft or hard tissue according to the therapeutic needs.

It is yet another objective of the present invention to provide devices that enable the user to choose a combination of parameters, such as different wavelengths and power settings, with movements on an electronic visual display that can detect the presence and location of a touch within the display area.

It is yet another objective of the present invention to provide devices and methods for medical and cosmetic applications that minimize the possibility of harming patients.

Briefly stated, the present invention provides improved, efficient devices and methods for medical and cosmetic applications, involving the delivery of laser energy to the tissue. In a preferred embodiment a portable, easy-to-use laser system comprises at least one laser source operating at one or more laser wavelengths; an electronic visual display having a n-dimensional input interface to set/select laser parameters; and at least one waveguide optically coupled to the laser source to convey laser radiation to a treatment site. The n-dimensional input interface is for input and selection of lasing parameters, which allows the selection of a combination of output wavelengths and of powers by simply touching the electronic visual display. The invention also provides a method of using the new laser system which comprises the steps of placing at least one waveguide in a preselected treatment site; selecting a combination of laser wavelengths and powers from a laser system by interacting with an electronic visual display; and irradiating the treatment site.

The above and other objects, features and advantages of the present invention will become apparent from the following description read in conjunction with the accompanying drawings (in which like reference numbers in different drawings designate the similar elements).

DETAILED DESCRIPTION OF PREFERRED EMBODIMENTS

Figure 1:
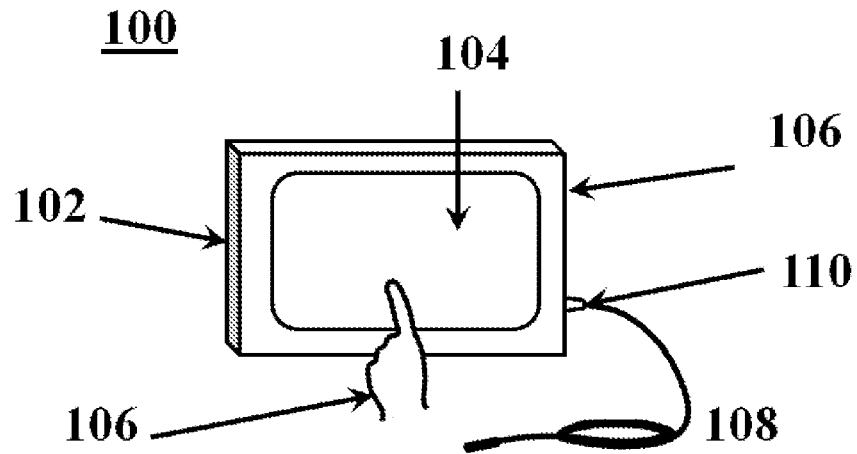
FIG. 1 depicts a preferred embodiment of present invention describing a laser system device for medical and cosmetic applications.

The invention described herein provides many advantages over prior art alternative devices and methods for medical and cosmetic applications concerning the use of laser energy. It provides simpler and more efficient devices an methods for a variety of medical and cosmetic applications including, but not limited to dermatology, ENT, gynecology, proctology, ophthalmology, phlebology, pneumology, gastroenterology, spinal disk surgery, thoracic surgery, general laser surgery, photodynamic therapy, lipo surgery and urology treatments. This new generation of laser systems enables incision, excision, vaporization, ablation, hemostasis, disruption/destruction, chromophore/photosensitizer activation, and/or coagulation to be performed selectively and accurately in soft or hard tissue according to the therapeutic needs. Furthermore, safety precautions are also included which help in minimizing the possibilities of harming patients while performing the treatments.

This invention further provides a user friendly, versatile laser system which can be used for a broad spectrum of applications, facilitating the physician's learning curve and providing the opportunity to choose between different laser energy delivery modes and/or to use individualized settings defined by the user in an easy, prompt way. Moreover, this technology provides a compact, space-saving design always needed and desired in a physician's office as well as low-maintenance and reliable laser sources.

A laser system for medical and cosmetic applications comprises at least one laser source operating at one or more laser wavelengths; an electronic visual display providing a n-dimensional input interface, wherein n is equal to 2 or more and at least 2 parameters are simultaneously set; and at least one waveguide coupled to the laser radiation source in order to deliver laser radiation at a preselected treatment site.

In one embodiment, the electronic visual display is a touch-sensitive screen which provides a 2-dimensional input interface and enables the user to two-dimensionally set the laser parameters by touching the display of the device with a finger, a passive object, such as a stylus, or any similar object known in the art.

In another embodiment, the laser parameters are selected by a three-dimensional input interface wherein the electronic visual display provides a cube space with depths and enables the user to three-dimensionally set the laser parameters by placing the finger close to the display of the device. The three-dimensional input interface allows the user to select the laser parameter by reading the distance of the finger from the screen and the bidimensional position on the screen. Some additional movement of the finger, like vibrating the fibertip rapidly, then fix the 3-dimensional point. Instead of the finger, the user can use a passive or an active object, such as a stylus, or any similar object known in the art for this purpose.

Similarly, other dimensions are included or excluded into or from the input interface, as long as the dimension of the input interface has at least two dimensions.

The laser source of the laser system comprises diode laser sources, ionic crystal laser sources, fiber laser emission sources, or other known in the art in different combinations. One of the remarkable features of this laser system is that when two laser wavelengths are emitted through the same output port, these are controlled completely independently of each other. The versatility of the system is also evident because the output of the laser system can be selected according to the therapeutic application, i.e. delivering a single wavelength or a combination of laser wavelengths and at powers that can be adjusted either independently or dependently among the selected wavelengths, all by selecting the desired combination using the n-dimensional input interface of the electronic visual display, for example by touching the screen of the device. The touch-sensitive screen is capable of establishing a combination of wavelengths and power settings by means of a single touch, a touch and drag movement, or in multiple touches.

In one embodiment, the output of the laser system is adjusted by choosing a mode wherein the laser source operates at a single wavelength. With a single laser wavelength, the user selects for example, the output peak pulse power and the on-off ratio of the pulse of the laser system for the chosen wavelength using a bidimensional input interface of the electronic visual display.

In another embodiment, the output of the laser system is adjusted by choosing a mode wherein the laser source operates at two wavelengths. When the laser system operates at two laser wavelengths concurrently, its enhanced characteristic is that the user can select a fixed total output power and easily define the proportion of the output power for each laser wavelength, by touching the touch-sensitive screen of the laser system, while maintaining a fixed total output power. Additionally, when the laser system operates at two laser wavelengths concurrently, the user can select the ratio between the two laser wavelengths and then, while maintaining the fixed wavelengths ratio, the user selects the desired total output power by touching the visual screen and the individual wavelength powers scale at the selected fixed ratio.

In another embodiment, when the laser system operates at two or more laser wavelengths, the user selects, via the 2-dimensional input interface, the output peak pulse power and the on-off ratio of the pulse for one wavelength first, and then, in sequence, selects the output peak pulse power and the on-off ratio of the pulse via the 2-dimensional input interface for the other wavelengths.

In another embodiment, the user finds and selects the appropriate laser wavelengths and power combination by placing their finger on the screen and moving it until the desired combination is fixed. The adjustment of these parameters is made via a touch-sensitive screen comprising a user-friendly menu system.

Apart from the irradiation power, and quantity and type of wavelengths, other parameters are also introduced via the n-dimensional input interface of the electronic visual display such as speed, treatment mode, quantity and type of switches, aiming beams, languages, and other parameters commonly used in laser treatments. At least two parameters or parameters' characteristics are simultaneously set with the n-dimensional input interface of the electronic visual display. The laser system also provides a plurality of treatment modes wherein a single mode can be used during the whole treatment, or different modes in a sequential manner, depending on the requirements of the specific treatment. The treatment modes comprise, but are not limited to, continuous wave mode, pulse mode, segment mode, signal mode, derma mode. The laser energy delivered according to these modes are controlled with one or more switches such as a foot-switch, handswitch or similar known in the art, preferably connected via a wireless connection. Generally, a treatment mode is selected according to specific therapies or in combination with the properties of appropriate application fibers.

In continuous wave mode, the laser continuously emits laser radiation at a selected power level. In pulse mode, the laser emits radiation at a selected peak pulse power level with a specified number of pulses and pulse format (pulse duration/pulse pause), or with a continuous series of pulses.

Signal mode is derived from the continuous mode and it is aimed for procedures in which the waveguide delivering the laser energy is moving, for example while it is withdrawn from the inside of a vein in endoluminal vascular treatments. In signal mode, the laser system indicates optimal movement speed of the waveguide via signal sounds. In an embodiment for endoluminal vascular treatments, the proper treatment speed is calculated from a combination of output and energy per signal, that has been calculated and selected according to target vein diameter.

The segment mode is also derived from the continuous mode and it is aimed for procedures in which the waveguide delivering the laser energy is moving and different segments of the treatment site need different treatments/powers. In this mode, the laser system indicates the movement speed of the waveguide via signal sounds and an additional visual support for the user during the procedure.

The derma mode, which is especially useful for dermatology treatments, is derived from the pulse mode, in which the laser system sets the required laser output for the selected power density in relation to a selected hand piece.

In a preferred embodiment, the signal mode and the segment mode are used for endoluminal vascular treatments in which these modes indicate via sound and/or visual signals the speed at which an optical fiber has to be pulled while irradiating the inside of a vein.

The laser system is intended for delivery of laser light to soft or hard tissue with at least one waveguide in contact or non-contact mode during surgical procedures, including via endoscopes, introducers, or catheters; or during non-surgical procedures such as in transdermal treatments. The waveguide is optically coupled to the laser source and conveys laser radiation to a preselected treatment site, determined in accordance with the therapeutic needs. Preferably, said waveguide is an optical fiber having selectable distal tip shapes, including a radial-emitting tip, a conically shaped tip, a circumferentially-emitting tip, a twisted shaped tip, a side-emitting tip, a bare tip, an off-axis tip, a double core tip, a flat tip, among others. These optical fibers are referred to as application fibers, which are coupled to the laser source and are selected according to the treatment to be performed with the laser system. Waveguides having multiple emission points are also available, such as, two or more radial emitting distal sections. Additionally, the laser system is further enhanced with one or more visible-light lasers acting as an aiming beam, which allows a better identification of the direction of the laser light while it is fired at the desired target.

One potentially dangerous drawback of prior art laser systems, is the possibility of coupling unsuitable optical fibers to the laser source which even if not reusable have already been used in other procedures, its valid lifetime has elapsed, or due to an improper size chosen it might cause an improper or unsafe laser energy dose delivery at the treatment site. Thus, in another embodiment, the laser system provided in this invention further comprises a special fiber connector for coupling the waveguide with the laser source. The fiber connector is equipped with an electronic signature for increased patient safety, because it prevents usage beyond the product's lifetime and other hazards caused by using unsuitable fibers with the laser.

Among the numerous safety features known in the art, this invention preferably includes, but is not limited to, a key switch/key code, an emergency laser stop, a remote interlock, a fiber interlock per laser output port, and a system for automatic detection of the light conductor. Nevertheless, other and additional safety features may also be included. When one or more critical safety condition is not met, the firing of the treatment laser firing is prohibited.

The laser system of this invention further comprises an integrated microprocessor which controls and monitors the fiber-coupled laser system with automatic power control.

A preferred embodiment is depicted in FIG. 1, showing laser system 100 for medical and cosmetic applications comprising laser source 102, operating at two laser wavelengths; a laser wavelength that is highly absorbed by blood or hemoglobin, and a laser wavelength that is highly absorbed by water; electronic visual, touch-sensitive display 104, which detects the presence and location of pressure caused by user's finger 106 in contact with electronic visual display 104 area; and radial-emitting optical fiber 108 bearing a connector equipped with an electronic signature, for delivering laser energy onto a preselected treatment site. For increasing patient safety and preventing from coupling unsuitable fibers to laser system 100, laser source 102 further comprises connector 110 equipped with an electronic signature for coupling radial-emitting optical fiber 108. Additionally, laser system 100 has a distinctive characteristic that its depth dimension is at least two, three or more times smaller than its width and/or height dimensions.

By choosing the appropriate combination of laser parameters, such as laser wavelengths and power settings, according to the therapeutic needs, the laser system of this invention performs selectively and accurately incision, excision, vaporization, ablation, hemostasis, disruption/destruction, chromophore-photosensitizer activation, and/or coagulation. Thus, a combined, enhanced and efficient therapeutic effect by using different laser wavelengths in a single, concurrent treatment can be obtained. The different degrees of incision, excision, vaporization, ablation, hemostasis, disruption/destruction, chromophore/photosensitizer activation, and/or coagulation are determined by the diverse combinations of laser wavelengths and powers, selected by or with the system.

Figure 2:
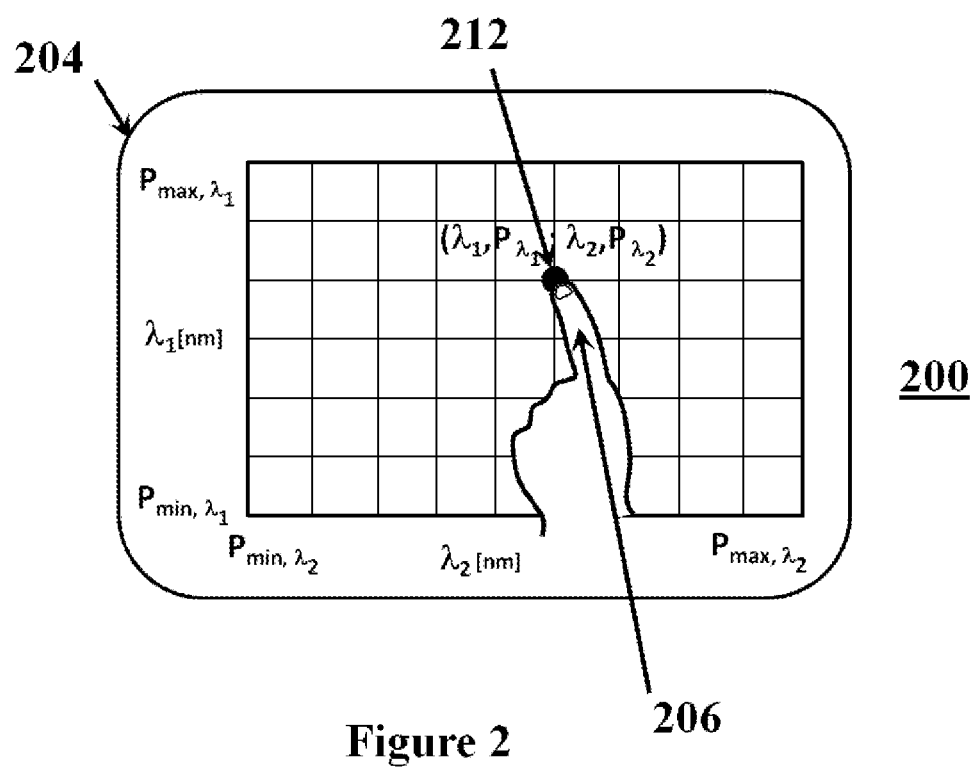
FIG. 2 shows a preferred embodiment of present invention where appropriate combination of wavelengths and power settings are selected on an electronic visual display.

FIG. 2 shows another embodiment of touch-sensitive display 204 which allows using finger 206 contact to choose the appropriate combination of wavelengths and power settings according to the therapeutic needs. By using finger 206 position within the display area to select appropriate options, different combinations of laser wavelengths and powers can be selected. In a preferred embodiment, finger 206 is in contact with display 204 and moves within display 204 until it reaches the desired combination of laser wavelengths and powers 212. Once combination of laser wavelengths and powers 212 is reached, finger 206 is taken off from display 204 and combination of laser wavelengths and powers 212 is fixed.

In one embodiment, the laser source of the laser system is a diode laser source that operates at one or two laser wavelengths, in the range of between about 600 nm to 800 nm. This laser system is for use in photodynamic therapy procedures, in which the laser wavelengths of the system and their combination of laser ratio and output power are chosen according to the laser wavelength absorbed either by an externally administered photosensitizer or an internal chromophore at the treatment site. The appropriate combination of wavelengths and power settings allows selective, accurate chromophore/photosensitizer activation.

In another embodiment, the laser system operates at two laser wavelengths in the range of between about 600 nm to 800 nm and has a three-dimensional input interface. The laser wavelength ratio is selected by placing the finger close to the display, and the relation of output power of both wavelengths is selected by the bidimensional position of the finger on the screen. The 3-D input interface reads the distance of the finger to the visual display and associates it with a specific wavelength ratio, and reads the position of the finger on the screen and relates it to a specific relation of output power of both wavelengths.

In other embodiments, the laser source of the laser system is a diode laser source that operates at one or two laser wavelengths, in the range of between about 900 nm to 2000 nm, particularly when blood and tissue irradiation are required for therapeutic treatment.

In one embodiment, the laser system operates at about 980±30 nm and/or at about 1350±50 nm, for use in thoracic surgeries with laser energy. Depending on the desired therapeutic effect, only one laser wavelength is delivered by the laser system, or both laser wavelengths are delivered concurrently. In case different degrees of coagulation, ablation, vaporization, excision and/or incision are desired, the laser system delivers both laser wavelengths simultaneously and the user can select just by touching the touch-screen of the laser system, e.g., either 1) a determined proportion of the laser wavelength's output power with a fixed total output power, or 2) a defined laser wavelength ratio with one of the possible corresponding total output powers available. In another embodiment, the laser system operates at about 980±30 nm and/or at about 1900±50 nm and either only one laser wavelength is delivered by the laser system, or both laser wavelengths are delivered concurrently, according to the desired therapeutic effect.

In another embodiment, the laser source operates at about of 1470±50 nm and/or about 980±30 nm. The laser system operates either at single laser wavelength or at both wavelengths together, and when both wavelengths are delivered concurrently their output powers can still be independently regulated. Endoluminal vascular treatments benefit, when the laser system operates at both wavelengths concurrently, in that the practitioner can select the combination of wavelengths ratio and total output power independently, depending upon whether the therapeutic effect requires more hemoglobin or water absorption at the treatment site. Preferably, the waveguide coupled to the laser system for endoluminal vascular treatments has a circumferentially-emitting tip allowing a homogeneous delivery of radiation to the blood vessel. This type of optical fiber usually has a round shield covering the distal tip which is sufficiently flexible to allow the optical fiber to bend upon passage through a tortuous vessel. Due to the round shape of this distal fiber tip, the treatment can often be performed without a separate guide wire reducing treatment times and simplifying the procedure.

In one embodiment, a method for medical and cosmetic applications comprises the steps of placing at least one waveguide in a preselected treatment site; selecting a combination of laser wavelengths and power for the laser system by touching an electronic visual display; and irradiating said treatment site. Once the waveguide is appropriately placed in a preselected treatment site, the user selects one combination of laser wavelengths and laser output powers by 'touching' the screen which is able to detect the presence and location of a touch within or position above the display area, for example with his finger, and moving the finger on the screen until the desired combination is chosen. Hence, the practitioner has the possibility to freely combine the power of two laser wavelengths and define the best mix of these parameters for a variety of applications with a doctor-friendly laser device.

In a preferred embodiment, the power of laser wavelengths of about 980±30 nm and 1470±50 nm are freely combined, in order to obtain different degrees of laser absorption by water and hemoglobin in the body, in accordance with the different degrees of therapeutic effects that are to be achieved i.e. incision, excision, ablation, coagulation, disruption/destruction, and vaporization. When used for endoluminal treatments, the waveguide coupled to the laser source preferably has a circumferential-emitting distal tip or a conically shaped distal tip as these emission patterns allow a more homogenous and uniform delivery of laser radiation, to the vein wall.

Additionally, different treatment modes are also available which include continuous wave mode, pulse mode, segment mode, signal mode, derma mode, as well as combinations of them.

Figure 3:
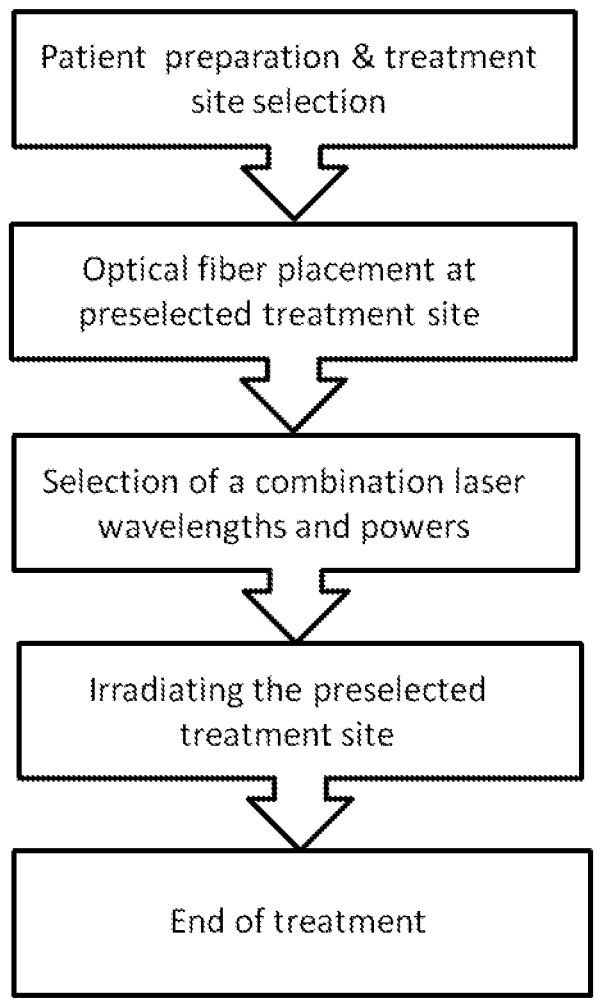
FIG. 3 shows a preferred embodiment, representing the steps of a method for medical and cosmetic treatments with the laser system of present invention.

FIG. 3 depicts the main steps of methods for medical and cosmetic applications using the new laser system.

The major advantages of this laser system to hospitals and patients are that the laser system is light and compact; it works in multiple applications due to the possibility of having one, two or more treatment wavelengths in one laser source unit; and that these different wavelengths and the laser parameters can be freely set/combined, solely with movements on an electronic visual display having an input interface which allows to set parameters multidimensionally. As a consequence, advantages of obtaining different degrees and a variety of therapeutic effects with a user friendly, easy-to-use, small device can be accomplished, while avoiding main drawbacks of the classic devices and techniques.

The present invention is further illustrated by the following examples, but is not limited thereby.

Example 1

A medical laser system which operates; at a single wavelength of about 980 nm, at a single wavelength of about 1470 nm, or at both wavelengths is used. At its proximal end, an optical fiber is coupled to the laser source and at its distal end, the fiber's radial-emitting tip is placed inside the greater saphenous vein. The general procedure has the patient placed in Trendelenburg position to distend the Greater Saphenous Vein. Local anesthesia is administered by infiltration with a 27 G needle at the point of percutaneous entry. Using ultrasound guidance, a percutaneous entry into the vein to be treated is obtained with a standard 18 Gauge×7 cm entry needle. Then a 0.035" to 0.038" guide wire is inserted into the entry needle and is gently advanced to the desired length, i.e. to stop at the starting treatment site.

After the guide wire is advanced to desired location the needle is removed proximally and an assembly comprising a 23 cm dilator inserted into a 11 cm 6 French sheath is threaded over guide wire and inserted through the puncture site into the vessel to be treated with a slight rotary motion. Then, the dilator and guide wire are removed together leaving the sheath in the vessel. The radial-emitting fiber is inserted through the sheath into the vein and is advanced gently through the vein using ultra sound guidance to 1 cm below the saphenofemoral junction, which is typically the initial treatment site. The location of the laser fiber tip can be confirmed using ultrasound guidance and by direct visualization of the red aiming beam of the laser fiber through the skin.

Now use of the touch-sensitive visual screen with two-dimensional control permits the simple, efficient setting/adjusting of laser parameters. With the laser system operating at both wavelengths concurrently, the practitioner places their finger on the touch-sensitive screen of the laser system, and by performing two dimensional movements on the screen, they select a combination of laser output powers for the wavelengths of about 980 nm and 1470 nm. To treat a vein 5 mm in diameter, practitioner selects a fixed total output power of 5 W and then by moving their finger on the screen selects the proportion of 980 nm and of 1470 nm, with a power of 1.6 W for the 1470 nm laser wavelength and 3.4 W for the 980 nm laser wavelength to treat the vein wall. Alternatively, the practitioner selects a predetermined proportion of 1470 nm and 980 nm laser wavelength, e.g. ⅓ of 1470 nm laser wavelength power and ⅔ of 980 nm laser wavelength power, and then moves his finger within the screen to select the total output power, choosing a total output power of 4 W. In this case, the laser system delivers 1.3 W of the 1470 nm laser wavelength power and 2.7 W of the 980 nm laser wavelength. After selecting the laser parameters, the sheath is removed before starting the laser emission. Laser emission is activated by depressing the footswitch. Simultaneously, radial emitting optical fiber is slowly withdrawn at a constant speed of about 2 mm per second, leading to vein's closure.

Example 2

One example of a laser system for medical applications, which enables incision, excision, vaporization, ablation, hemostasis, or coagulation of soft tissue in ear, nose and throat and oral surgery (otolaryngology), dental procedures, arthroscopy, gastroenterology, general surgery, dermatology, plastic surgery, podiatry, urology, gynecology, neurosurgery (peripheral nervous system), pulmonary surgery, cardiothoracic surgery, ophthalmology and vascular treatments such as the endovenous occlusion of the greater saphenous vein, is as follows. As before the laser source emits two coherent laser radiations of wavelength of 980 nm±30 nm, and 1470 nm±30 nm. It also has two aiming beams, one operating at 532 nm±10 nm and the other operating at 635 nm±10 nm, each of whose intensity can be adjusted by the user, too. The laser system has a maximum laser output power of 15 W for the 1470 nm wavelength and 30 W for the 980 nm wavelength. In the case of both wavelengths operating together, the output power can be adjusted by selecting a combination of the laser wavelengths (980 nm and 1470 nm) and of output powers by employing the touch-sensitive screen which is able to detect the presence and location of a touch within the display area. The range of 3 to 10 W is used especially for endoluminal vascular treatments with the laser system coupled to a waveguide having a circumferential-emitting distal tip or a conically shaped distal tip, or a waveguide with multiple radially emitting points.

In addition to setting and using personalized settings selected on the touch-sensitive, visual display of the laser device, the laser system delivers radiation under several other laser delivery modes. One example is a pulse mode in which the laser system emits radiation at the selected power level with the specified number of pulses and pulse format (pulse duration/pulse pause) as long as the footswitch is pressed. Typically the pulse duration/pause is in the range of 0.01-60 sec, and the number of pulses can be selected between 1 and a maximum of 100 pulses. A continuous series of pulses can be delivered as long as the footswitch is depressed, or the pulse procedure can be repeated as long as the footswitch is depressed or until the defined number of pulses is reached.

Different optical fibers with diverse tips and fiber diameters can be connected, provided these are recognizable/allowable by the proximal fiber connector at the laser source, equipped with an electronic signature. This laser system has approximate dimensions of 28 cm high, 37 cm wide and 9 cm in depth; and weighs approximately 7 kg. For safety in use, the laser system should be mounted on a stable support to avoid movement and can include additional means known in the prior art for providing physical stability to the laser system.

Example 3

The laser system of this embodiment is used for photoselective vaporization of the prostate in office and outpatient settings leading to excellent results in tissue ablation and hemostasis and low complication rates. The laser source of the laser system operates at a wavelength of about 980±30 nm, and at a wavelength of about 1470±30 nm. The laser power source in this embodiment is somewhat larger in order to produce the much higher output powers required for efficient use in prostate treatments. The user selects a fixed output power of 150 W (or 200 W) and then by moving his finger on the screen as described earlier, user selects the proportion of 980 nm and of 1470 nm. For a total output power of 150 W a power of 50 W for the 1470 nm laser wavelength and of 100 W for the 980 nm laser wavelength is selected. That is a ratio of 1:2 with total power of 150 W. Now a typical procedure for treating Benign Hyperplasic Prostates (BPH) follows.

A 24 Fr continuous flow cytoscope fitted with a 30° telescope and visual obturator is used. The outer sheath of the cytoscope is inserted into the urethra through the visual obturator followed by a laser bridge. The bladder is distended with iced saline solution and the scope is forwarded so its tip is placed close to the bladder neck. An optical fiber having an off-axis irradiating tip for use in contact mode is inserted until it reaches the tip of the scope. Then, taking care not to irradiate the bladder neck itself, beginning from the bladder neck the laser is activated and the prostate tissue is vaporized from the surface of the median lobe, sweeping the fiber slowly and continuously in a gentle rotation movement in a 5 o'clock to 7 o'clock direction, keeping the fiber in contact with prostatic tissue. Once the median lobe is reduced, the treatment proceeds with the right lobe and/or the left lateral lobe. Once the treatment is completed and a predetermined quantity of prostatic tissue has been removed, the cytoscope is retracted. Patients are then checked for hemostasis with irrigation off, fitted with a Foley catheter which is removed the next day. With ability in the present laser system to simply select and set laser parameters using beforehand the touch-sensitive visual screen allows the practitioner to devote more attention to monitor the progress and performance of the irradiation treatment for safety and efficacy.

In other preferred embodiments, the touch-sensitive display system is used for input of multiple device options and functions, including but not limited to display options, video selection, user settings, service settings, remote service, and video section.

Having described preferred embodiments of the invention with reference to the accompanying drawings, it is to be understood that the invention is not limited to the precise embodiments, and that various changes and modifications may be effected therein by skilled in the art without departing from the scope or spirit of the invention as defined in the appended claims.

What is claimed is:

1. A laser system for medical and cosmetic applications comprising: a. at least one laser source operating at one or more laser wavelengths; b. an electronic visual display having a two-dimensional input interface comprising a rectangular touch-sensitive screen having a vertical edge and a horizontal edge to set/select laser parameters; c. at least one waveguide; d. means to optically connect said laser source to said at least one waveguide; wherein said waveguide is optically coupled with the laser source to convey laser radiation to a treatment site; and wherein a first laser parameter is displayed along a vertical edge of the touch-sensitive screen and a second laser parameter is displayed along a horizontal edge of the touch-sensitive screen, the touch-sensitive screen being configured so that the two laser parameters are simultaneously set by touching the touch-sensitive screen at a single point.

2. The laser system according to claim 1, wherein said laser source operates at one or more laser wavelengths, which are highly absorbed by water and/or hemoglobin.

3. The laser system according to claim 2, wherein said laser source operates at a range of wavelengths between about 900 nm to 2000 nm.

4. The laser system according to claim 3, wherein said laser source operates at about 980.+−.30 nm and at a laser wavelength selected from the group, of about 1350.+−.50 nm, of about 1470.+−.50 nm, and of about 1900.+−.50 nm.

5. The laser system according to claim 1, wherein said laser source operates at one or more laser wavelengths, which are highly absorbed by externally administered photosensitizers or internal chromophores.

6. The laser system according to claim 5, wherein said laser source operates at a range of wavelengths between about 600 nm to 800 nm.

7. The laser system according to claim 1, wherein said touch-sensitive screen is used to set a combination of laser parameters according to the therapeutic needs enabling the laser system to perform an action selected from the group of incision, excision, vaporization, ablation, hemostasis, disruption/destruction, chromophore/photosensitizer activation, coagulation, or a combination of these.

8. The laser system according to claim 1, wherein said laser parameters are the wavelengths and power settings.

9. The laser system according to claim 1, wherein said laser parameters are selected from the group consisting of power, speed, treatment mode, quantity and type of switches, quantity and type of wavelengths, pulse format, and aiming beams.

10. The laser system according to claim 1, further comprising a fiber connector for coupling the waveguide with the laser source wherein said fiber connector is equipped with an electronic signature for increased patient safety.

11. The laser system according to claim 1, wherein said waveguide is an optical fiber.

12. The laser system according to claim 11, wherein said optical fiber has distal tip shapes selected from the group consisting of radial-emitting tip, conically shaped tip, circumferentially-emitting tip, twisted shaped tip, side-emitting tip, bare tip, off-axis tip, double core tip, and flat tip; and with one or more emission points.

13. The laser system according to claim 1, further comprising a plurality of treatment modes selected from the group of continuous wave mode, pulse mode, segment mode, signal mode, derma mode and combinations of these.

14. The laser system according to claim 1, for use in dermatology, ENT, gynecology, proctology, ophthalmology, phlebology, pneumology, gastroenterology, spinal disk surgery, thoracic surgery, general laser surgery, photodynamic therapy, lipo surgery and urology treatments.

15. The method for medical and cosmetic applications, using a laser system as described in claim 1, comprising the steps of: 1. placing said at least one waveguide at a preselected treatment site; 2. selecting a combination of laser parameters from said laser system by using the touch-sensitive screen and 3. irradiating said treatment site through said at least one waveguide.

* * * * *